United States Patent
Brown et al.

(10) Patent No.: US 12,275,906 B2
(45) Date of Patent: Apr. 15, 2025

(54) HYDRODEOXYGENATION OF PHENOLIC LIPIDS AND RENEWABLE HYDROCARBON FUELS PRODUCED THEREFROM

(71) Applicant: Renewable Energy Group, Inc., Ames, IA (US)

(72) Inventors: Jared Brown, Ankeny, IA (US); Ramin Abhari, Bixby, OK (US); Martin Haverly, Ames, IA (US); David A. Slade, Ames, IA (US); Dhananjay Ghonasgi, Bartlesville, OK (US)

(73) Assignee: Renewable Energy Group, Inc., Ames, IA (US)

( * ) Notice: Subject to any disclaimer, the term of this patent is extended or adjusted under 35 U.S.C. 154(b) by 0 days.

(21) Appl. No.: 18/478,125

(22) Filed: Sep. 29, 2023

(65) Prior Publication Data
US 2024/0124791 A1 Apr. 18, 2024

Related U.S. Application Data

(60) Provisional application No. 63/377,573, filed on Sep. 29, 2022.

(51) Int. Cl.
*C07C 65/05* (2006.01)
*C10L 1/02* (2006.01)
(Continued)

(52) U.S. Cl.
CPC .............. *C10L 1/026* (2013.01); *C07C 65/05* (2013.01); *C25B 1/04* (2013.01); *C25B 15/08* (2013.01); *C10L 2200/0446* (2013.01)

(58) Field of Classification Search
CPC .. C07C 65/05; C10G 3/42; C10G 3/45; C10G 3/46; C10G 3/50; C10L 1/026;
(Continued)

(56) References Cited

U.S. PATENT DOCUMENTS 2,482,760 A 9/1949 Goebel
2,664,429 A 12/1953 Goebel
(Continued)

FOREIGN PATENT DOCUMENTS

WO WO-2023233151 A1 * 12/2023 ............. C08G 59/26

OTHER PUBLICATIONS

International Search Report and Written Opinion for PCT/US2023/075564 dated Jun. 24, 2024.
(Continued)

*Primary Examiner* — Ellen M McAvoy
*Assistant Examiner* — Chantel Graham
(74) *Attorney, Agent, or Firm* — Nyemaster Goode, P.C.

(57) ABSTRACT

The invention relates to renewable hydrocarbons, and more particularly to biomass-based diesel fuel produced in a process including hydrodeoxygenation (HDO) of phenolic lipids. The process may generally include combining a phenolic lipid and a hydrocarbon diluent to provide a hydrocarbon-diluted phenolic lipid then subjecting the hydrocarbon-diluted phenolic lipid to hydrodeoxygenation in a reactor to provide a reactor effluent including a hydrodeoxygenated phenolic lipid. The hydrodeoxygenated phenolic lipid is separated from the reactor effluent.

23 Claims, 5 Drawing Sheets

(51) Int. Cl.
*C25B 1/04* (2021.01)
*C25B 15/08* (2006.01)

(58) Field of Classification Search
CPC ...... C10L 1/04; C10L 1/08; C10L 2200/0446; C25B 1/04; C25B 15/08; C25B 15/081; Y02P 30/20
See application file for complete search history.

(56) References Cited

U.S. PATENT DOCUMENTS

| | | | |
|---|---|---|---|
| 7,968,757 B2 | 6/2011 | Abhari et al. | |
| 8,026,401 B2 | 9/2011 | Abhari et al. | |
| 8,932,453 B2 | 1/2015 | Yao et al. | |
| 9,404,064 B2 | 8/2016 | Guay et al. | |
| 11,118,133 B2 | 9/2021 | Slade et al. | |
| 2008/0296167 A1* | 12/2008 | Davidson | C25B 15/00 205/334 |
| 2016/0200995 A1* | 7/2016 | Cui | C09K 8/52 44/307 |
| 2018/0291254 A1 | 10/2018 | Leinweber et al. | |
| 2022/0081626 A1* | 3/2022 | Myllyoja | C10G 3/46 |
| 2024/0124791 A1 | 4/2024 | Brown et al. | |

OTHER PUBLICATIONS

Paschke, R.F.; Wheeler, D.H.; The Journal of the American Oil Chemists' Society, Jun. 1949; pp. 278-283.
Index of Commercial Antioxidants and Antiozonants; The Goodyear Tire & Rubber Co.; 1999.
Rasmus Egeberg and coworkers (Top Catal (2009) 52:229-240).
Jerzy Walendziewski and co-workers (Fuel Processing Technology 90, 2009, 686-691).
Rasmus Egeberg and coworkers (Petroleum Technology Quarterly, 2nd Quarter, 2010, 1-11).
P. Dhar and co-workers (Hydrocarbon Processing, Jan. 2018; 25-28).

* cited by examiner

HYDRODEOXYGENATION OF PHENOLIC LIPIDS AND RENEWABLE HYDROCARBON FUELS PRODUCED THEREFROM

This application claims priority from U.S. Provisional Application No. 63/377,573 filed Sep. 29, 2022, which is incorporated herein by reference in its entirety.

FIELD OF THE INVENTION

The present invention relates to renewable hydrocarbons, more particularly to renewable hydrocarbon fuels, and most particularly to biomass-based diesel fuel.

BACKGROUND OF THE INVENTION

Hydroprocessing of fatty acids/glycerides for production of Renewable Diesel (RD) fuel has been described in the prior art; e.g., U.S. Pat. Nos. 8,026,401 and 7,968,757. The RD feedstocks described in the prior art encompass most conventional lipids such as animal fats and vegetable oils. As described in the cited prior art and many other related references, RD is produced in two conversion steps. In the first step, a hydrodeoxygenation (HDO) reaction converts the fatty acid/glyceride molecules to n-paraffins in the diesel boiling range (150-380° C.). The glycerol backbone of the fatty acid glycerides (i.e., a triglyceride or diglyceride) is transformed into propane during HDO. The reaction generates water, CO, and $CO_2$ as the main byproducts. To convert the C16+ n-paraffin "wax" and improve cloud point and other low temperature flow properties, the straight-chain n-paraffins in the HDO product are converted to mainly methyl-branched paraffins in the second step. This second step is referred to as "catalytic dewaxing" or "hydroisomerization" (HI).

Due to its isoparaffinic composition (n-paraffins and iso-paraffins, with virtually no naphthenics or aromatics), RD has a very high cetane number, typically above 84. This makes it an excellent fuel for compression ignition engines.

However, fatty acid derived RD has certain disadvantages as well. Typical RD density values of around 780 kg/m³ are lower than petroleum diesel (typically about 880 kg/m³) and biodiesel (around 850 kg/m³). Since higher mass density generally translates to higher energy density, a hydrocarbon composition of higher density is desired for renewable diesel.

Co-hydroprocessing of conventional lipids with petroleum fractions has been disclosed in the prior art. For example, co-hydroprocessing of 10% and 20% rapeseed oil with straight-run diesel/light gas oil has been described by Jerzy Walendziewski and co-workers (*Fuel Processing Technology* 90, 2009, 686-691). In a more recent study, P. Dhar and co-workers report co-processing of 5-15% palm and jatropha oils with straight-run gas oil (*Hydrocarbon Processing*, Jan. 2018; 25-28). These studies broadly describe the conversion chemistry of lipids with mainly C16 and C18 fatty acids to n-paraffins in the C15-C18 range, and highlight the deterioration of the treated diesel low-temperature properties (i.e., cloud point, CFPP, pour point) with increase in feed lipid content. Furthermore, the petroleum refineries targeted for co-hydroprocessing are typically not set up to handle the carbonic acid corrosion (formed by the water and $CO_2$ byproducts described earlier herein). Co-hydroprocessing of conventional lipids with petroleum fractions has been also shown to impact the hydrodesulfurization (HDS), hydrodenitrogenation (HDN), and hydrodearomatization (HDA) activity of the catalyst as noted by Rasmus Egeberg and coworkers (*Petroleum Technology Quarterly*, 2$^{nd}$ Quarter, 2010, 1-11, as well as *Top Catal* (2009) 52:229-240) and Jane Yao et al. (U.S. Pat. No. 8,932,453). In particular, the CO co-product has been shown to inhibit the activity of the catalyst for HDS, HDN and HDA reactions, especially for Cobalt-Molybdenum (CoMo) hydrotreating catalysts commonly used in petroleum refining. Inhibition of Nickel-Molybdenum (NiMo) catalyst by CO is less pronounced. The result of the inhibition is that to reach the specifications of sulfur in the product the co-processing operations have to be conducted at higher reactor temperatures resulting in possible shortening of the catalyst cycle length.

Due to the paraffinic nature of the fatty acid HDO products, these have high cloud points (typically between 20 and 22° C.) and require a high degree of isomerization to reduce the cloud point values by 20-40° C. for use as neat fuel. The main HDO product of typical fatty acid lipids is n-octadecane (C18 n-paraffin) with melting point of 28° C. By comparison, n-dodecyl cyclohexane (a C18 alkyl cyclohexane) has a melting point of 9° C. The melting points of alkyl aromatic compounds is even lower, with n-dodecyl benzene (a C18 alkyl benzene) reported to have a melting point of −7° C.

Another disadvantage of RD processes based on fatty acid glyceride feeds relates to the expense and capital costs for equipment. Separation and recovery of the propane coproduct adds a number of process units and equipment to the plant that are not directly related to the manufacture of RD.

A further process disadvantage is related to the oxygen content of the feedstock. With over 11 wt. % oxygen in fatty acid feedstock, a significant amount of hydrogen is used to remove that oxygen as a water effluent. Furthermore, fatty acid deoxygenation invariably results in formation of carbon oxides (CO and $CO_2$) in addition to water, requiring provisions for separation of these non-condensable gas phase byproducts from recycled hydrogen.

One class of biomass-based liquid feedstocks that potentially address some of these deficiencies is phenolic bio-oils. As recognized by persons skilled in the art, phenols undergo hydrodeoxygenation to produce aromatics (e.g., benzene; 876 kg/m³) and naphthenics (e.g., cyclohexane; 779 kg/m³) which are more energy dense than equivalent carbon number n-paraffins (e.g., n-hexane; 655 kg/m³) or iso-paraffins (e.g., 2-methyl pentane; 653 kg/m³). Production of phenolic bio-oils from lignocellulose biomass has been disclosed in the prior art. However, the prior art also highlights the challenges of processing such phenolic bio-oils including incomplete deoxygenation and relatively rapid catalyst deactivation.

Thus, there remains an unmet need for a renewable diesel having a higher energy density and a lower capital cost process.

We have identified a class of lipids that addresses the aforementioned needs. This class of lipids is referred to as phenolic lipids. These phenolic lipids are structurally similar to conventional non-phenolic fatty acid lipids but have the aforementioned advantages provided by the phenol functionality. The similarities and differences between conventional fatty acid lipids and phenolic lipids may be observed by the illustrative molecular structures I and II for stearic acid and anacardic acid, respectively.

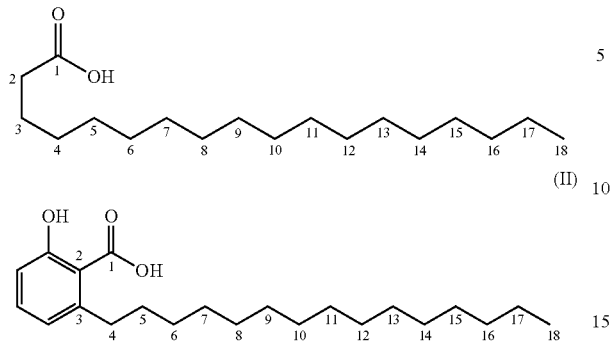

Structure II thus represents a lipid having a fused phenol group attached to the second and third carbon from the carboxylic acid carbon of a fatty acid molecule.

Accordingly, phenolic lipids have a carboxylic acid group at the phenol's ortho position and an alkyl/alkenyl chain at the meta position. Phenolic lipids also include structures such as catechol (1,2-dihydroxybenzene) instead of phenol (hydroxybenzene).

Prior art discloses that the carboxylic acid group may be removed by heat treatment (including pyrolysis, mechanical processing, and distillation) to provide a thermally decarboxylated phenolic lipid. Removal of the carboxylic acid group provides an additional benefit of reducing or eliminating the yield of CO byproduct during HDO. This effect can be particularly beneficial for co-processing with petroleum feedstocks whereby the inhibition of HDS activity by CO can be reduced and a higher inclusion of the renewable feedstock realized.

Conventional lipids are prone to oxidation. Autoxidation is effected by atmospheric oxygen with the process initiated by radical reactions involving unsaturated fatty acids. The primary products formed are hydroperoxides, which then break down in a series of complex reactions to form a number of secondary products. These secondary products may include alcohol and carbonyl compounds, as well as polymers/oligomers. U.S. Pat. No. 2,482,760 describes a method to separate oleic acid from polyunsaturated fatty acids (with similar boiling temperatures) by thermally polymerizing the latter. U.S. Pat. No. 2,664,429 discloses an alternate method for thermal polymerization of fatty acids. Thermal polymerization of unsaturated fatty acid esters is also disclosed in the prior art (e.g., Paschke, R. F.; Wheeler, D. H.; *The Journal of the American Oil Chemists' Society*, June 1949; pp 278-283). The oxidative stability of fats and oils is measured using the Active Oxygen Method (AOCS Cd 12-57) or the Rancimat Method (AOCS Cd 12b-92).

Prior art teaches that alkyl phenols are effective antioxidants. Hindered phenols, such as butyrated hydroxy toluene (BHT) are general purpose anti-oxidants for a variety of products including fuels and oils. Similar compounds (e.g., hydroquinones) have also been used commercially as shortstops for inhibiting polymerization reactions (see for example, *Index of Commercial Antioxidants and Antiozonants*; The Goodyear Tire & Rubber Co.; 1999).

SUMMARY

In one aspect of the present technology, renewable diesel fuels with densities (at 15.6° C.) of 780 kg/m³ or greater and cloud points of 18° C. or less are produced in a process including hydrodeoxygenation (HDO) of phenolic lipids. In embodiments, the phenolic lipid is decarboxylated prior to HDO conversion.

In a different aspect of the present technology, the phenolic lipid HDO process utilizes green hydrogen from water electrolysis. In some embodiments, the phenolic lipid is subjected to pre-hydrogenation. In other embodiments, pre-hydrogenated phenolic lipid is used as a carrier for the green hydrogen. In still further embodiments, the pre-hydrogenated phenolic lipid is subjected to HDO process to produce a renewable diesel. In additional embodiments, the pre-hydrogenated phenolic lipid is blended with conventional non-phenolic fatty acid lipids prior to HDO conversion to renewable diesel. In some embodiments, the RD from HDO conversion is hydroisomerized to further reduce cloud point. In other embodiments, the RD from HDO conversion is hydrocracked to renewable jet fuel or sustainable aviation fuel (SAF) and renewable gasoline.

In embodiments, the phenolic lipid is used to provide anti-oxidant and polymerization inhibition properties to conventional fatty acid based lipids.

DETAILED DESCRIPTION

Figure 1:
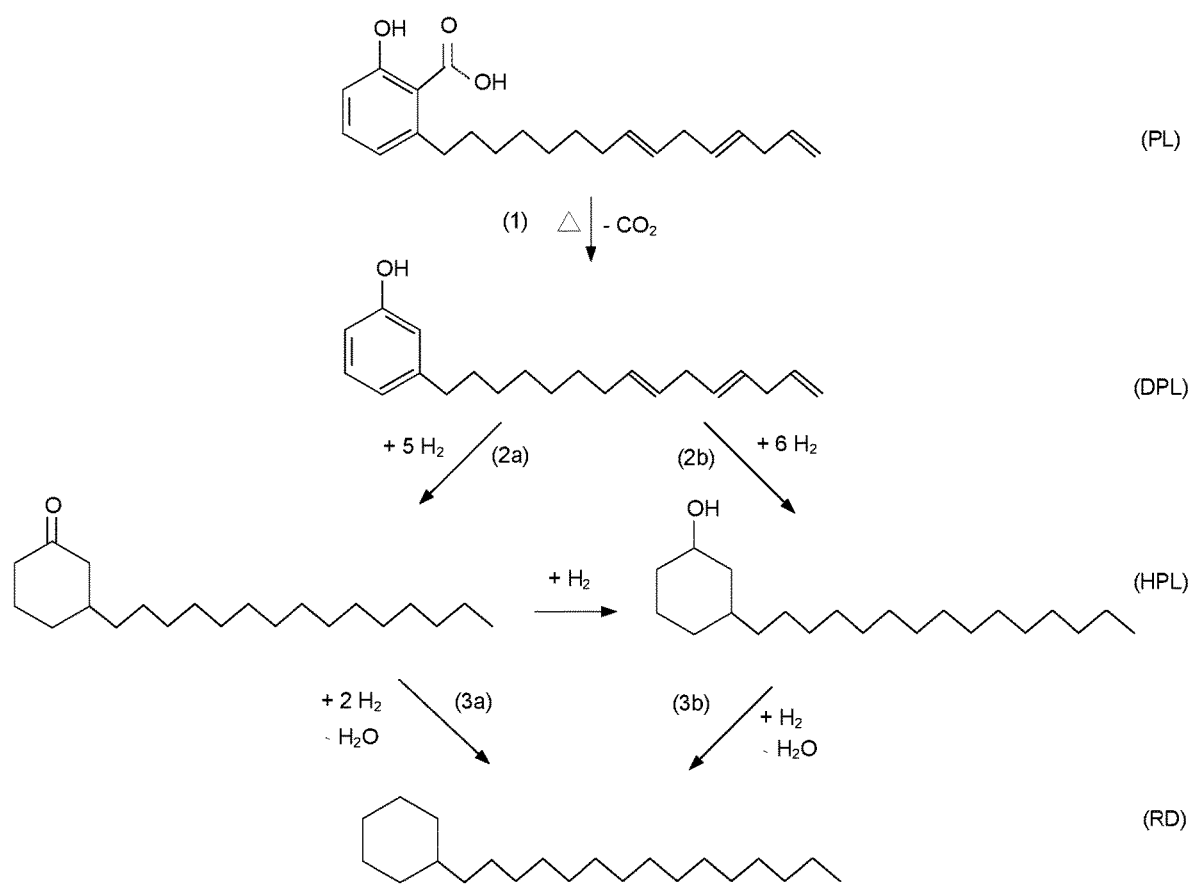
FIG. 1 depicts an illustrative reaction pathway for conversion of phenolic lipids to hydrocarbon fuel components.

Decarboxylation of Phenolic Lipids: Phenolic lipids (PL) are readily decarboxylated with thermal treatment to provide a decarboxylated phenolic lipid (DPL). FIG. 1 provides an illustrative conversion pathway whereby a typical PL compound, anacardic acid, is decarboxylated into corresponding DPL, cardanol. Any number of conditions and apparatus that provide heating of the PL to temperatures in the 250-550° F. in the general absence of air (to avoid oxidation) may be practiced to achieve conversion of PL to DPL. The decarboxylation systems and apparatus include agitated reactors with heating jacket for heating with steam or hot oil. Alternatively, vessels with steam injection may be employed. Alternatively, reactive distillation may be employed. As recognized by those skilled in the art, many variations exist and may be employed to optimize decarboxylation.

Hydrogenation of Phenolic Lipids: The DPL undergoes hydrogenation through saturation of the benzene ring and the carbon-carbon double bonds in the alkyl group. In the case of cardanol, the alkyl group is a 15-carbon chain with 1, 2, or 3, carbon-carbon double bonds. As shown in FIG. 1, the hydrogenated phenolic lipid (HPL) may be an akylcyclehexanone or an alkylcyclohexanol depending on the extent of functional group reduction. Hydrogenation is often carried out under relatively high pressures (from 100 to 2,000 psig) at temperatures in the 250 to 500° F. range. Preferred catalysts include palladium on alumina, or reduced nickel on same supports or as a sponge metal catalyst (e.g., RANEY catalysts). DPL may be hydrogenated in both batch or continuous reactors, using fixed-bed or slurry catalyst reactor systems.

Hydrodeoxygenation of Phenolic Lipids: The HPL compounds may undergo HDO to hydrocarbons according to Eqs. 3a and 3b in FIG. 1. For phenolic lipid hydrodeoxygenation, a sulfided molybdenum or tungsten catalyst with hydrogenolysis activity is preferred. Promoters for HDO catalysts include nickel and cobalt. In the present invention, the reactor conditions are selected such that the PL can be converted to RD in one step (combining Eqs. 1, 2a, 2b, 3a, and 3b). The HDO temperatures for the present invention are in the 500 to 700° F. under $H_2$ partial pressures between 100-2,500 psia. In embodiments, the DPL is used as HDO feed. In embodiments, the PL/DPL hydrodeoxygenation to RD is conducted in one reactor wherein the RD has an oxygen content less than 0.1 wt. %, less than 4% aromatics, and a bromine index above 70.

A First Embodiment of the Present Technology

Figure 2:
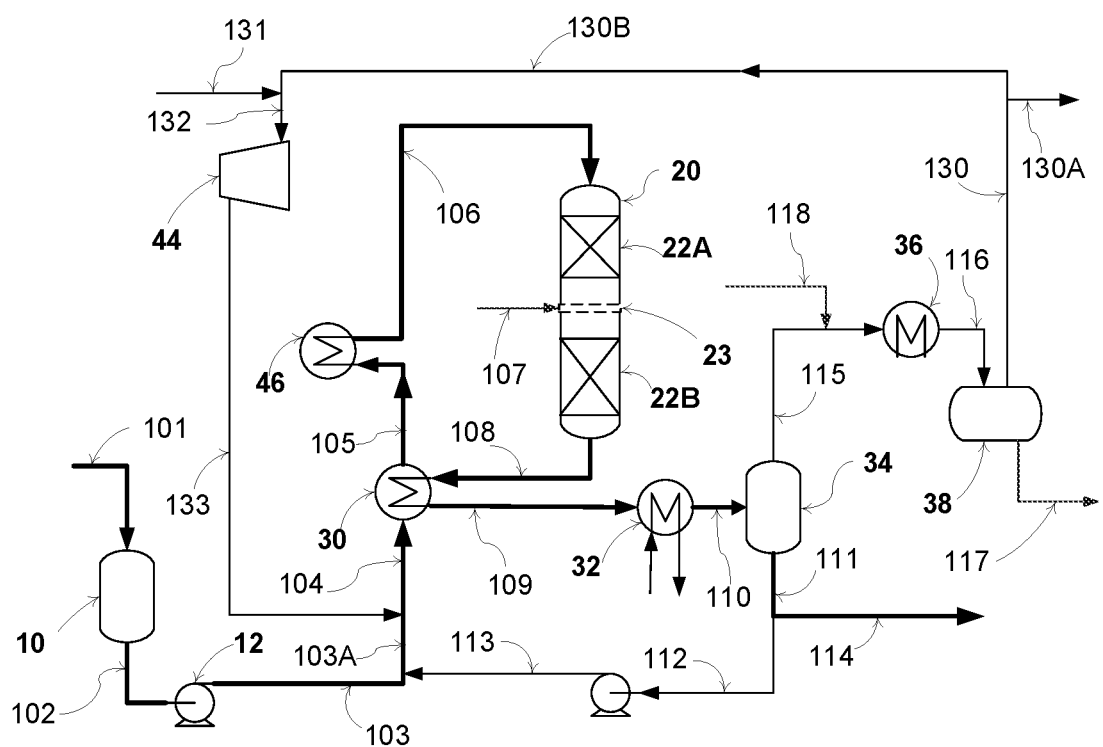
FIG. 2 is a process flow diagram showing an embodiment of a method for producing renewable diesel from phenolic lipids.

Referring to the process embodiment depicted in FIG. 2, a biological feedstock 101 comprising a phenolic lipid is directed to a surge drum 10. The phenolic lipid may be plant, bacterial, fungal or a combination thereof. In one exemplary embodiment, the phenolic lipid is cashew nut shell liquid (CNSL). CNSL is a component of the cashew fruit's nut. It is a dark reddish-brown liquid housed in the soft honeycomb shell of the nut that is released when the shell is broken. CNSL represents a byproduct of the cashew industry. In some embodiments, the phenolic lipid includes anacardic acid, cardol, cardanol, and 2-methyl cardol.

In other embodiments, the biological feedstock 101 includes decarboxylated phenolic lipid. In embodiments, the feedstock 101 may be decarboxylated CNSL (also referred to as $2^{nd}$ boil CNSL or Technical CNSL). In embodiments, the decarboxylated phenolic lipid is at least 50 wt. % cardanol.

In some embodiments, the feedstock 101 is pretreated according to lipid pretreatment methods described in the prior art; e.g., U.S. Pat. Nos. 11,118,133 and 9,404,064, which are hereby incorporated by reference. The purpose of pretreatment is to remove phosphorus, silicon, and metal contaminants from the feedstock 101. The need for pretreatment is more important when the phenolic lipid has not been decarboxylated as these typically have higher concentrations of the cited contaminants.

In embodiments where the phenolic lipid has not been decarboxylated, provisions may need to be taken in surge drum 10 to ensure a homogenous biological feedstock is maintained. Such provision include mechanical agitation or a recirculation pump as familiar to persons skilled in the art. Additional provisions may include stabilization additives such as polymerization inhibitors, surfactants, peroxide scavenger, and anti-oxidant.

The surge drum 10 provides a pump suction liquid 102 for pressurization and transfer as a pressurized feedstock 103. The pressurized feedstock 103 is optionally combined with a hydrocarbon diluent, such as a hydrocarbon product recycle stream 113 as shown in FIG. 2. A hydrocarbon diluted feedstock 103A is combined with a pressurized hydrogen 133 to provide a heat exchanger feedstock inlet 104. The heat exchanger feedstock inlet 104 is heated through a feed-effluent exchanger 30 to provide a heat exchanger feedstock outlet 105. The heat exchanger feedstock outlet 105 is further heated in heater 46 to provide a heated reactor feed 106.

The heater 46 is preferably a shell and tube exchanger with the reactor feed flowing through the tubes with a heat transfer fluid flowing through the shell side. The heated reactor feed 106 has a temperature between 500 and 700° F. In embodiments, the heated reactor feed has a temperature of 520° F., 540° F., 560° F., 580° F., 600° F., 620° F. , 640° F., 660° F., 680° F., or a value between any two of these temperatures. For example, in a preferred embodiment, the heated reactor feed is between 560 and 660° F. Although a shell and tube heat exchanger is described for this embodiment of the method, those skilled in the art recognize that other types of heat exchanger or heating methods may also be used as recognized by persons skilled in the art. For example, in a preferred embodiment the hydrocarbon product recycle stream 113 may be heated in a fired heater to a temperature that when combined with pressurized feedstock 103 achieves the heated reactor feed temperatures described herein, thus avoiding heating of the phenolic lipid component in a heat exchanger.

Returning to FIG. 2, the heated reactor feed 106 enters a hydrodeoxygenation (HDO) reactor 20 comprising a fixed-bed catalyst. The HDO reactor 20 is maintained at a pressure between 500 and 2,700 psig. In embodiments, the reactor is maintained at 600 psig, 800 psig, 1,000 psig, 1,200 psig, 1,400 psig, 1,600 psig, 1,800 psig, 2,000 psig, 2,200 psig, 2,400 psig, 2,600 psig, or a value between any two of these pressures. In a preferred embodiment, the HDO reactor 20 is maintained between 1,600 and 2,400 psig.

The pressurized feedstock 103 is introduced to the reactor at a liquid hourly space velocity (LHSV) between 0.3 and 6.0 $h^{-1}$ (vol/h of feedstock 103 per vol of catalyst). The pressurized hydrogen 133 is at a ratio relative to feedstock 103 that is between 2,000 SCF/Bbl and 10,000 SCF/Bbl. In a preferred embodiment, the reactor operates at LHSV values between 0.5 and 5.0 $h^{-1}$ and gas-to-oil ratios between 4,000 and 8,000 SCF/Bbl.

The HDO reactor 20 includes at least one bed of a sulfided catalyst comprising molybdenum or tungsten. Preferred catalysts further include nickel or cobalt promoters. Such catalysts include sulfided nickel-molybdenum (NiMo), nickel-tungsten (NiW), or cobalt-molybdenum (CoMo) on alumina or silica-alumina supports. It should be understood by one of ordinary skill in the art that any catalyst or combination of catalysts may be used in the present invention so long as the catalyst system functions in accordance with the present invention as described herein.

To maintain the active metal sulfide functionality of the catalyst despite absence or very low (<40 wppm) concentrations of organic sulfur in most biological feedstocks, the combined feedstock 103 may be supplemented with a sulfur compound that decomposes to hydrogen sulfide when heated and/or contacted with a catalyst. Two preferred sulfur compounds are dimethyl disulfide and carbon disulfide. Preferred concentration of these in the pressurized feedstock 103 is from about 100 to about 2,000 ppm by weight sulfur.

The HDO reactor 20 is operated at a weighted average bed temperature (WABT) between 550 to about 650° F. WABT is commonly used in fixed bed, adiabatic reactors to express the "average" or "equivalent isothermal temperature" of the reactor that accounts for the nonlinear temperature profile between the inlet and outlet of the reactor according to the equation below.

$$WABT = \sum_{i=1}^{N}(WABT_i)(Wc_i)$$

$$WABT_i = \frac{T_i^{in} + 2T_i^{out}}{3}$$

In the equation, i represents the bed number and $Wc_i$ is the weight fraction of total catalyst in bed i. In the FIG. 2 embodiment, the HDO reactor 20 includes two beds; bed 22A and bed 22B. If bed 22A and bed 22B have the same weight of catalyst and have an inlet temperature of 560° F. and outlet temperature of 640° F. (due to adiabatic temperature rise from the exothermic reactions in the HDO reactor), they will each have a $WABT_1=WABT_2=[550° F.+2(640° F.)]/3=610°$ F., and the total WABT=0.5(610° F.)+0.5(610° F.)=610° F. In FIG. 1, a quench hydrogen gas 107, which is preferably a slip stream from compressed hydrogen 133, is introduced between the two reactors to lower the bed 22B inlet temperature. The HDO reactor 20 is operated at WABT values between 580 to 640° F. In embodiments, the WABT is 580° F., 590° F., 600° F., 610° F., 620° F., 630° F., 640° F., or maintained in a range between any two of these temperatures. In a preferred embodiment, the WABT is maintained between 590 and 630° F. It has surprisingly been observed that such a temperature range achieves the desired balance between high phenolic oxygen removal and moderate saturation for maintaining low cloud point compared to fully saturated hydrocarbons.

The reactor effluent 108 is cooled through the feed-effluent exchanger 30 to provide a partially cooled reactor effluent 109 that is further cooled in the reactor effluent cooler 32. The cooled reactor effluent 110 is at temperature of about 250 to about 400° F. and has liquid and vapor phase HDO products in addition to unconverted hydrogen gas. A gas/vapor phase 115 is separated from a liquid hydrocarbon phase 114 in a separator 34. The high-pressure separator 34 operates at the reactor exit pressure (minus pressure drop across the pipe runs and exchangers). The gas/vapor phase 115 includes hydrogen and the water vapor byproduct of the HDO reaction. This is cooled in a condenser 36 to provide a two-phase fluid that is separated in cold separator drum 38. In embodiments, a wash water 118 is introduced upstream of the condenser 36 to wash any solid deposits that may form on the condensing surface. The condensed water 117 is thus removed from a gas phase 130 that is mainly hydrogen. The gas phase 130 is mostly recycled through hydrogen compressor 44. In order to maintain purity of pressurized hydrogen 133 at a hydrogen purity target value between 80 and 99 mol. % concentration, a fraction of the recycled gas 130 is purged as bleed gas 130A as makeup hydrogen 131 is provided to make up for chemical hydrogen consumption (as well as solubility and other losses) and maintain the gas to oil ratios described previously herein. In embodiments wherein the phenolic lipid has not been decarboxylated, the decarboxylation occurs in the HDO reactor and therefore more gas (containing $CO_2$ and CO contaminants) needs to be purged as bleed gas 130A. When the phenolic lipid in the biological feedstock 101 is substantially decarboxylated (e.g., when $2^{nd}$ boil CNSL is the phenolic lipid) a much lower fraction of the recycle gas needs to be purged as bleed gas 130A, typically less than 2% of the total pressurized hydrogen 133. In some embodiments using decarboxylated phenolic lipid, the bleed gas 130A is between 0% and 1% of the total pressurized hydrogen 133 during normal operating conditions.

Returning to separator 34, the liquid hydrocarbon phase 114 is optionally transferred to a stripper (not shown) where dissolved gas phase byproducts such as $H_2S$ and water are removed to provide a hydrocarbon suitable for use as diesel fuel or a diesel fuel blendstock in compression ignition engines. The hydrocarbon fuel composition comprises mainly of alkylcyclohexane and methyl alkylcyclohexane wherein the alkyl group is a C9-C21 straight chain hydrocarbon. The hydrocarbon composition includes less than 0.1 wt. % oxygen and up to 4 wt. % aromatics. The hydrocarbon composition has a density (at 15.5° C.) of at least 780 kg/m³ and a cloud point of 18° C. or less, preferably 16° C. or less, with a Bromine Index of 70 or higher.

In embodiments, the liquid hydrocarbon phase 114 is directed to another hydroprocessing reactor (not shown) wherein the hydrocarbon is subjected to hydrocracking and isomerization reactions. In some embodiments, the hydrocracked/isomerized product is fractionated to provide a low cloud point diesel with cloud point values of −5° C. or less, and/or jet fuel with a freeze point of −40° C. or less.

A Second Embodiment of Present Technology

As observed from Eqs. 2(a)/2(b) and 3(a)/3(b) in FIG. 1, the hydrogenation/hydrodeoxygenation of phenolic lipids to the hydrocarbon fuel compositions of the present invention, may advantageously be conducted without production of propane, $CO/CO_2$, and other non-condensable gas phase byproducts. As such, the reaction may be conducted without need for gas cleanup and recycle, including in a batch reactor system. Also observed from Eqs. 2(a)/2(b) and 3(a)/3(b), the conversion reaction of the typical phenolic lipid molecule cardanol to hydrocarbon fuel consumes 7 moles of hydrogen (14.1 g) per mole of n-pentadecylcylo-hexane product (294.6 g). If the hydrogen were to be provided by intermittent renewable power (via water electrolysis), the technology would represent an efficient method for "storing" and "carrying" the renewable electricity for use as transportation fuel as described below.

Figure 3:
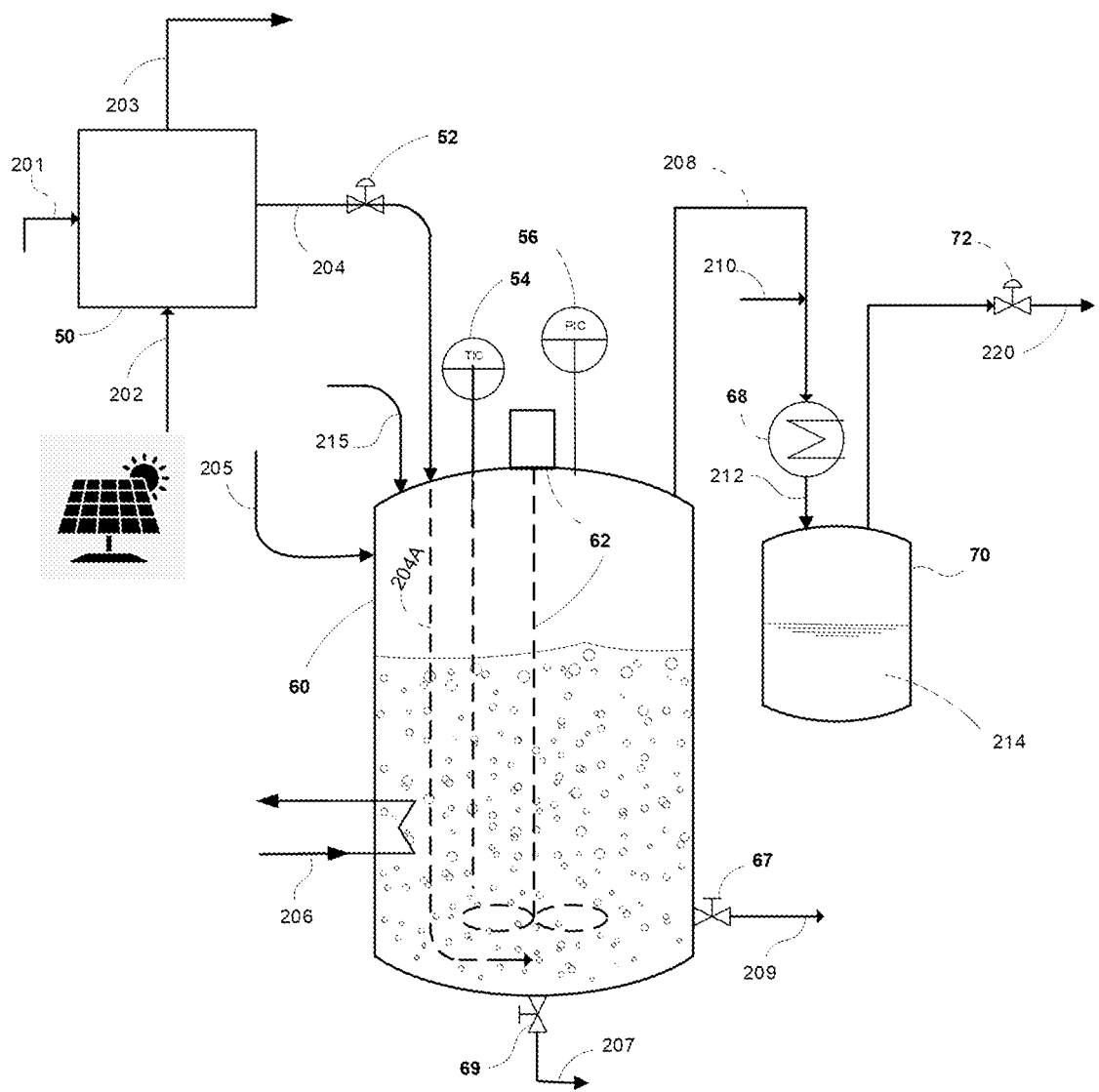
FIG. 3 is a process flow diagram showing an embodiment of a method for conversion of phenolic lipids in a batch reactor.

Referring to FIG. 3, a water electrolysis unit 50 is equipped with an anode and a cathode separated by a membrane (not shown) as described in the prior art. The water electrolysis unit or electrolyzer is supplied by a water 201 and direct current electricity 202 to convert the water molecules to a hydrogen 204 (from the cathode) and oxygen 203 (over the anode). Typically, 10-20 kg $H_2$ is generated per MW of electric power. In embodiments, the electricity 202 is supplied by a photoelectric power station. In other embodiments, the electricity 202 is provided by a wind turbine and an inverter. The electrolyzer 50 is equipped with a compressor (not shown) to raise the pressure of the hydrogen from near atmospheric pressure to 100 psig or greater. In embodiments, the hydrogen 204 is supplied at a pressure between 100 and 2000 psig. In embodiments, the compressor is a multi-stage compressor. Since the electricity 202 is available intermittently (e.g., during daylight for the photoelectric power station embodiment), the hydrogen 204 is not available continuously. When available, a supply valve 52 is opened to a batch reactor 60 which has been pre-charged with a phenolic lipid feedstock through a conduit 205. The hydrogen disperses in the pre-charged feed through a hydrogen sparger 204A.

The batch reactor 60 is a pressure vessel designed to carry out hydrogenation reactions, preferably in the slurry mode using the same type of catalysts described previously for the continuous fixed-bed HDO reactor embodiment. Preferred catalysts for the batch slurry reaction are of a smaller size, typically with an equivalent particle size of 1.3 mm or less. The reactor is preferably equipped with an agitator system 62 to suspend the catalyst and disperse the hydrogen in the precharged feedstock. The batch reactor 60 also includes provisions for heating and cooling via a heat transfer fluid circulating through a heating/cooling coil 206. In some embodiments, the heating is provided through a reactor jacket (not shown), while the cooling is provided through cooling coils. Other reactor systems may be used for the batch reactor 60 as readily appreciated by persons skilled in the art and disclosed in the prior art literature about hydrogenation apparatus. These include the Buss Loop Reactor and the hollow-shaft gassing agitator reactor. In the Buss Loop Reactor, a recirculation pump and an external heat exchanger are provided with a nozzle to achieve intimate gas/liquid/catalyst mixing without a mechanical agitator. In the hollow-shaft gassing agitator reactor, the hydrogen is dispersed into the reactor through the agitator itself.

In embodiments, the pre-charged feed in the batch reactor 60 is a decarboxylated CNSL. Catalyst may be added to the precharged reactor as a slurry in oil or water through conduit 215. In preferred embodiments, the catalyst is pre-sulfided NiMo catalyst in a C10-C20 hydrocarbon. The concentration of catalyst in the precharged feedstock is between 1 and 20 wt. %, preferably between 2 and 10 wt. %.

The reactor is equipped with provisions for temperature indication/control 54 (e.g., through the heat transfer fluid 206) and pressure indication/control 56 (through hydrogen supply valve 52 and backpressure control valve 72). As such, the reactor is maintained at a pressure between 500 and 2,000 psig and a temperature between 500 and 650° F. In a preferred embodiment, the reactor is operated a pressure at 500-1000 psi and 580-640° F.

As the phenolic lipid undergoes hydrogenation and hydrodeoxygenation, hydrogen is consumed and additional hydrogen is provided through the hydrogen supply valve 52 to maintain pressure. In the meantime, water byproduct is accumulated in condenser drum 70 through condensation of the water vapor in the reactor head space vapor 208 in condenser 68.

A condensed water 214 accumulates in the condenser drum 70 during the batch reaction cycle. In embodiments, the water 214 is used to provide some of the water supplied to electrolyzer 50.

The reaction is complete when virtually no more hydrogen is consumed (no change in reactor pressure). At that point, the agitator system 62 is turned off and the catalyst is allowed to settle to the bottom of the reactor heal. The clarified liquid product layer is then discharged by opening valve 67 through conduit 209 which is directed to a polishing filter (not shown) to remove any suspended catalyst and catalyst fines. The filtered hydrocarbon product includes mainly alkylcyclohexane and methyl alkylcyclohexane and the alkyl group is a C9-C21 straight chain hydrocarbon. The hydrocarbon composition includes less than 0.1 wt. % oxygen and up to 4 wt. % aromatics. The hydrocarbon composition has a density (at 15.5° C.) of at least 780 kg/m$^3$ and a cloud point of 18° C. or less, preferably 16° C. or less, with a Bromine Index of 70 or higher.

After product discharge, a new load of decarboxylated phenolic lipid feed may be charged to the reactor 60 in preparation of the next availability of electrolyzer 50 (e.g., next morning's power generation from the photoelectric solar power station). Depending on feed contaminants, periodically a complete discharge of a spent catalyst slurry 207 via drain valve 69 may be required for regeneration or disposal.

The hydrocarbon product may be used as a carbon neutral diesel or diesel fuel blendstock (with the phenolic lipid carbon and hydrogen formed naturally through photosynthesis and the hydrodeoxygenation reaction conducted with renewable power). This exemplary embodiment also provides a solution to the challenges of baseload electric energy storage.

A Third Embodiment of Present Technology

In this exemplary embodiment, a conventional lipid feedstock is blended with 0.5 to 10 wt. % phenolic lipid prior to hydrodeoxygenation.

In the embodiment, the blending is performed during transfer of the feedstocks to a blended feedstock storage tank. The phenolic lipid provides the conventional lipid with improved oxidative stability. As a result, the phenolic lipid minimizes the secondary reactions resulting from formation of hydroperoxides thus improving processability (e.g., reduced corrosion due to formation and evaporation of lighter carboxylic acids, and reduced fouling due to thermal polymerization). Since volatile carboxylic acids such as formic and acetic acids are byproducts of fatty acid oxidation, the roof of the tanks containing conventional fatty acid based lipids tends to corrode causing iron and other corrosion products to contaminant the contents of the tank. The present embodiment of the disclosed technology mitigates such corrosion and contamination of conventional lipid feedstocks.

A test method for quantifying oxidative stability of conventional lipids is the Rancimat technique (basis for Oxidative Stability Index measurement according to AOCS Cd 1b-92). In this test method, the lipid is heated to a temperature in the 80-160° C. range and subjected to accelerated oxidation via an air sparge. The air off of the sample is passed through a deionized water container wherein the conductivity is continuously measured. The volatile organic acid byproducts formed during oxidation are dissolved in water and contribute to a rise in conductivity, thereby marking the onset of oxidation. The time it takes before oxidation is observed is known as induction time, and typically ranges from 1 hr. to 20 hrs. depending on the type of lipid and the test temperature. The shorter the induction time, the more susceptible the lipid is to oxidation.

In embodiments, the blended feedstock has about 1 wt. % phenolic lipid and 99 wt.% conventional lipid. In other embodiments, the phenolic lipid is $2^{nd}$ boil CNSL, and the conventional lipid feedstock includes, but is not limited to an animal fat, animal oil, microbial oil, plant fat, plant oil, vegetable fat, vegetable oil, grease, or a mixture of any two or more combinations thereof. Plant and/or vegetable oils include, but are not limited to, corn oil, inedible corn oil, babassu oil, carinata oil, soybean oil, canola oil, coconut oil, rapeseed oil, tall oil, tall oil fatty acid, palm oil, palm oil fatty acid distillate, jatropha oil, palm kernel oil, sunflower oil, castor oil, camelina oil, seaweed oil, oils from halophiles, and mixtures of any two or more combinations thereof. These may be classified as crude, degummed, and RBD (refined, bleached, and deodorized) grade, depending on level of pretreatment and residual phosphorus and metals content. However, any of these grades may be used in the present technology. Animal fats and/or oils as used above includes, but is not limited to, inedible tallow, edible tallow, technical tallow, floatation tallow, lard, poultry fat, poultry oils, fish fat, fish oils, and mixtures of any two or more combinations thereof. Greases may include, but are not limited to, yellow grease, brown grease, waste vegetable oils, restaurant greases, trap grease from municipalities such as water treatment facilities, spent oils from industrial packaged food operations, and mixtures of any two or more combinations thereof. Depending on level of pretreatment, such biorenewable lipid feedstock may contain between about 1 wppm and about 100 wppm phosphorus, and between about 1 wppm and about 100 wppm total metals (mainly sodium, potassium, magnesium, calcium, iron, and copper). The conventional lipid may also contain up to 20 wt. % free fatty acid. The conventional lipid may include about 1 wt. %, about 2 wt. %, about 3 wt. %, about 4 wt. %, about 5 wt. %, about 6 wt. %, about 7 wt. %, about 8 wt. %, about 9 wt. %, about 10 wt. %, about 11 wt. %, about 12 wt. %, about 30 wt. %, about 32 wt.%, about 34 wt. %, about 36 wt. %, about 38 wt. %, about 40 wt. %, about 13 wt. %, about 14 wt. %, about 15 wt. %, about 16 wt. %, about 17 wt. %, about 18 wt. %, about 19 wt. %, or any range including and/or in between any two of these values.

The blended feedstock with phenolic lipid provides better oxidative stability compared to the conventional feedstock as measured by AOCS Cd 12b-92 Rancimat Method. In certain embodiments, the blended feedstock of the present invention has an induction time greater than 10 hrs. at a test temperature of 110° C. according to AOCS Cd 12b-92. In embodiments, the blended feedstock has an induction time greater than 12 hrs. at a test temperature of 110° C. according to AOCS Cd 12b-92.

The blended feedstock comprising phenolic lipid may be stored in carbon steel storage tank for further treatment and hydrodeoxygenation as described earlier for the first embodiment.

A Fourth Embodiment of the Present Technology

A decarboxylated phenolic lipid is introduced to a petroleum hydroprocessing unit at an inclusion rate of about 1 to about 20 wt. %. In other embodiments, the hydroprocessing unit is a diesel hydrotreater wherein straight-run diesel from a crude oil distillation unit is desulfurized. In preferred embodiments, the decarboxylated phenolic lipid is a $2^{nd}$ boil CNSL with less than 3 wppm phosphorus, less than 2 wppm phosphorus, or less than 1 wppm phosphorus. In these embodiments, the corresponding total metals in the $2^{nd}$ boil CNSL are less than 3 wppm, less than 2 wppm, or less than 1 wppm. The diesel hydrotreater includes a bed or beds of CoMo and/or NiMo catalyst and is operated at WABT values in the range of 630 to 750° F. and pressures between 100 and 2,400 psig (typically 200-1.000 psig). The straight run diesel has a sulfur content of up to 0.6 wt.%, typically in the 0.1-0.5 wt.% range. In embodiments, the straight run diesel feed is partially or completely replaced by light gas oil, or with cracked stocks such as light vacuum gas oil or light cycle oil that have sulfur levels as high as 1.3 wt. %., or in the 0.6 to 1.3 wt. % range. The diesel hydrotreater is operated to provide a hydrotreated diesel with 15 wppm sulfur or less, preferably 10 wppm sulfur or less. In embodiments, the hydrotreated diesel has a sulfur content of 5-10 wppm and a biomass carbon content of 1-20 wt. % as measured by standard test method ASTM D6866. The hydrodeoxygenation of the biomass component is achieved while avoiding formation of CO and $CO_2$ byproducts, thus avoiding inhibition of HDS and HDN activity, and formation of carbonic acid in the water byproduct.

EXAMPLES

Example 1

Two identical pilot plant reactors were loaded in identical manner with two beds of catalyst. The top bed included 8 cc of a low activity Mo catalyst, and the bottom bed was loaded with 20 cc of a high activity NiMo catalyst. Each catalyst bed was diluted with inert glass beads of 70-100 mesh size at a 1:1 ratio by volume.

The two catalysts were in oxide form when loaded and reduced to active sulfide form during startup. The sulfiding procedure has a low temperature hold at around 400° F. and a high temperature hold (after $H_2S$ breakthrough was observed) at 650° F.

Store-bought canola oil was used to confirm catalyst activity in each reactor prior to switching to the phenolic lipid feedstocks. Both reactors operated at 1 $H^{-1}$ LHSV, 3:1 solvent-to-oil ratio (with SOLTROL 220 as solvent), 1800 psi hydrogen pressure and a similar stoichiometric excess of hydrogen (with actual hydrogen to phenolic lipid ratio of around 8,600 SCF/Bbl).

Two different phenolic lipid feedstocks were used: (1) crude cashew nut shell liquid (CNSL), and (2) $2^{nd}$ boil CNSL (decarboxylated and distilled CNSL). The crude CNSL was subjected to a pretreatment step prior to blending with canola oil. The pretreatment step included a citric acid wash and centrifugation as generally described in the prior art (e.g., U.S. Pat. No. 9,404,604). Both feedstocks were diluted with canola oil to 10 wt. % CNSL in the mixed lipid.

The 10 wt. % $2^{nd}$ boil CNSL in canola had less than 1 ppm phosphorus and metals (combined) and only 25 ppm organic nitrogen. The 10 wt. % pretreated crude CNSL in canola by contrast had substantially higher concentrations of these contaminants, with 30 ppm potassium, 5 ppm sodium, and 167 ppm organic nitrogen.

The reactors were operated isothermally at conditions of different temperatures as summarized in Table 1. The hydrocarbon phase from the steady-state HDO product was analyzed for residual oxygen, cloud point, aromatics content, and bromine index. The oxygen analysis was conducted using the Fast Neutron Activation Analysis (FNAA) with detection limit of 0.02 wt. %.

TABLE 1

Selected physical and chemical properties[a] of HDO products of Example 1.

| | Reactor Temperature (° F.) | | | | |
|---|---|---|---|---|---|
| | 600 | 625 | 650 | 650 | 650 |
| Feedstock[b] | 2$^{nd}$ boil CNSL blend with canola oil | | | Crude CNSL blend with canola oil | Canola Oil |
| Reactor temperature (° F.) | 600 | 625 | 650 | 650 | 600 |
| Oxygen content (wt. %) [FNAA] | <0.02 | <0.02 | <0.02 | <0.02 | <0.02 |
| Cloud point (° C.) [D5773] | 3.3 | 3.7 | 5.1 | 9.1, 3.5[c] | 4.9 |
| Bromine index [D2710] | 87 | 75 | 69 | | |
| Aromatic hydrocarbons (wt. %) [D6591] | <4 | <4 | <4 | | |
| Mono- | <4 | <4 | <4 | | |
| Di- | <0.1 | <0.1 | <0.1 | | |
| Tri- | <0.1 | <0.1 | <0.1 | | |
| Poly- | <0.1 | <0.1 | <0.1 | | |

Notes:
[a]Test method indicated in brackets; all results from the same reactor unless stated otherwise.
[b]All reactor feedstocks diluted with 3:1 solvent.
[c]Result from second reactor system.

As observed from Table 1, HDO of feedstocks comprising both crude and 2$^{nd}$ boil (decarboxylated) CNSL according to the present technology produced a hydrocarbon with no detectable oxygen at all reactor temperatures tested. According to the bromine index, saturation of the phenolic lipid based hydrocarbons increased with temperature with an apparent increase in hydrocarbon cloud point. A similar correlation has not been reported for HDO hydrocarbons from conventional non-phenolic fatty acid lipids. The optimum HDO conditions for producing a hydrocarbon fuel from phenolic lipids that has a lower cloud point than hydrocarbons from non-phenolic fatty acid lipids therefore appears to be with a WABT of 600-620° F.

Example 2

A sample product of hydrodeoxygenation of 2$^{nd}$ boil CNSL from Example 1 was submitted for analysis by GC with Mass Spectrometer detector to identify the reaction products. The analysis was performed with approximately a 10× dilution of the sample in heptane. The GC instrument and operating conditions are indicated below.

Figure 4:
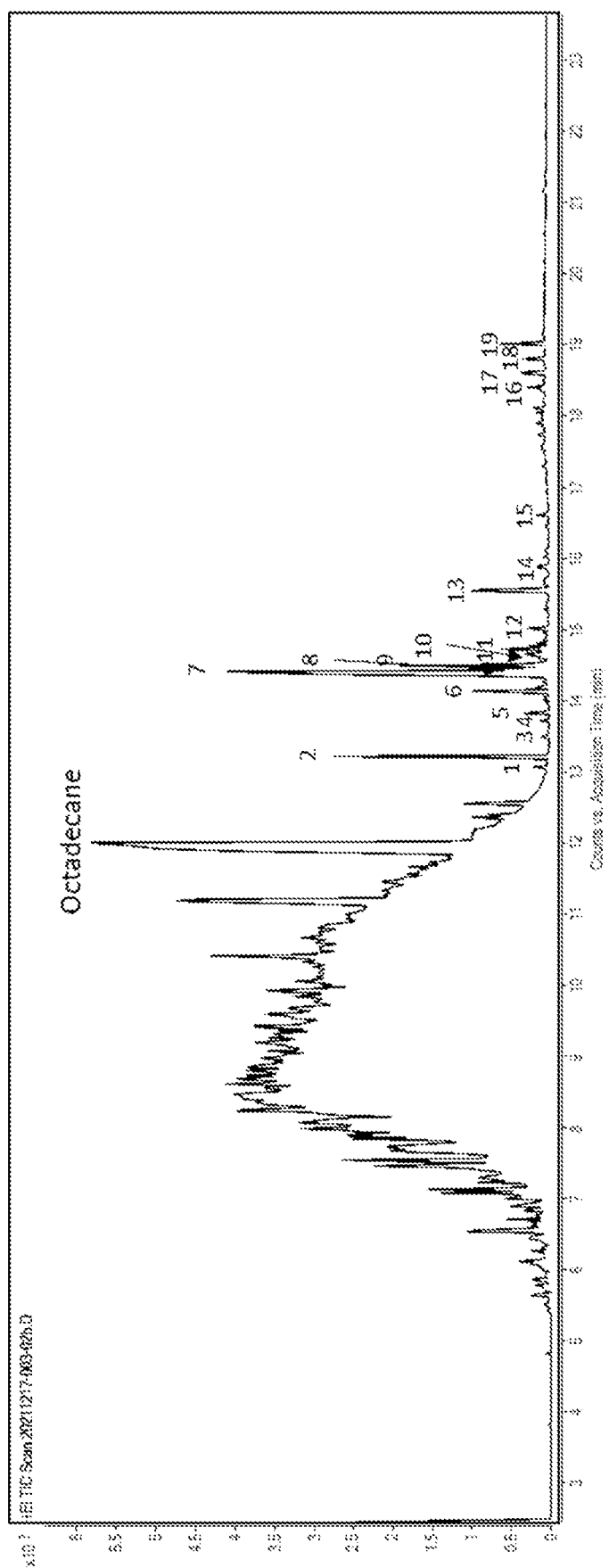
FIG. 4 is a chromatogram from a gas chromatography-mass spectrometry (GCMS) instrument showing product peaks in connection with Example 2.

Agilent 7890 GC and 5977B GC
Column: J&W HP-5 ms GC Column, 30 m, 0.25 mm, 0.25 mm, Agilent 19091S-433
Column flow: 1 mL/min
Inlet: Split, 20:1 split ratio, 250° C.
Oven: 45° C., ramp 15° C./minute to 325° C., hold for 5 minutes).
Injection volume: 1 µL The chromatogram generated in this experiment is shown in FIG. 4 with product peaks indicated by Numbers 1-19. The peaks associated with the SOLTROL solvent and canola oil HDO conversion (i.e., octadecane, heptadecane, hexandecane, and pentadecane) are not indicated by numbers.

Table 2 provides the identification of each product species according to highest probability match with the National Institute of Standards and Technology (NIST) mass spec database library. As observed in Table 2, the major product compound (Peak 7) is identified as n-pentadecyclohexane. Pentadecyl benzene (Peak 9) is observed as a minor product. Both of these are associated with hydrodeoxygenation of cardanol. The C20-C22 paraffins (eicosane, heneicosane, docosane) may include products of canola oil HDO. The C24+ hydrocarbons among the reaction products (Peaks 16-19) are associated with hydrodeoxygenation of sterols (which may be present as minor unsaponifiable matter in lipids).

TABLE 2

The identification table for GC Peak Numbers of FIG. 4.

| Peak Number | Retention Time | NIST ID | Formula | Probability* (%) |
|---|---|---|---|---|
| 1 | 13.066 | n-tridecylcyclohexane | C19H38 | 28.8 |
| 2 | 13.213 | Eicosane | C20H42 | 55.9 |
| 3 | 13.485 | 2,4-dimethyl-eicosane | C22H46 | 45.9 |
| 4 | 13.715 | Tetradecyl-cyclohexane | C20H40 | 38.1 |
| 5 | 13.819 | Heneicosane | C21H44 | 36.1 |
| 6 | 14.133 | n-Pentadecylcyclohexane | C21H42 | 44.4 |
| 7 | 14.405 | n-Pentadecylcyclohexane | C21H42 | 46.0 |
| 8 | 14.447 | Docosane | C22H46 | 24.1 |
| 9 | 14.489 | Pentadecyl-benzene | C21H36 | 63.0 |
| 10 | 14.656 | Oxalic acid, di(cyclohexylmethyl) ester | C16H26O4 | 9.71* |
| 11 | 14.719 | Henicosanal | C21H42O | 22.8 |
| 12 | 15.012 | Tricosane | C23H48 | 40.9 |

TABLE 2-continued

The identification table for GC Peak Numbers of FIG. 4.

| Peak Number | Retention Time | NIST ID | Formula | Probability* (%) |
|---|---|---|---|---|
| 13 | 15.535 | n-Heptadecylcyclohexane | C23H46 | 44.8 |
| 14 | 15.87 | Cyclohexane, 1,3,5-trimethyl-2-octadecyl- | C27H54 | 18.1* |
| 15 | 16.602 | Pentacosane | C25H52 | 12.4* |
| 16 | 18.402 | Coprostane | C27H48 | 33.3 |
| 17 | 18.611 | Cholestane | C27H48 | 24.7 |
| 18 | 18.799 | Stigmastane | C29H52 | 85.6 |
| 19 | 19.008 | Stigmastane | C29H52 | 92.1 |

Note:
*The higher the probability the more reliable the identification. Probabilities below 20% are very low and should not be relied upon.

Example 3

Figure 5:
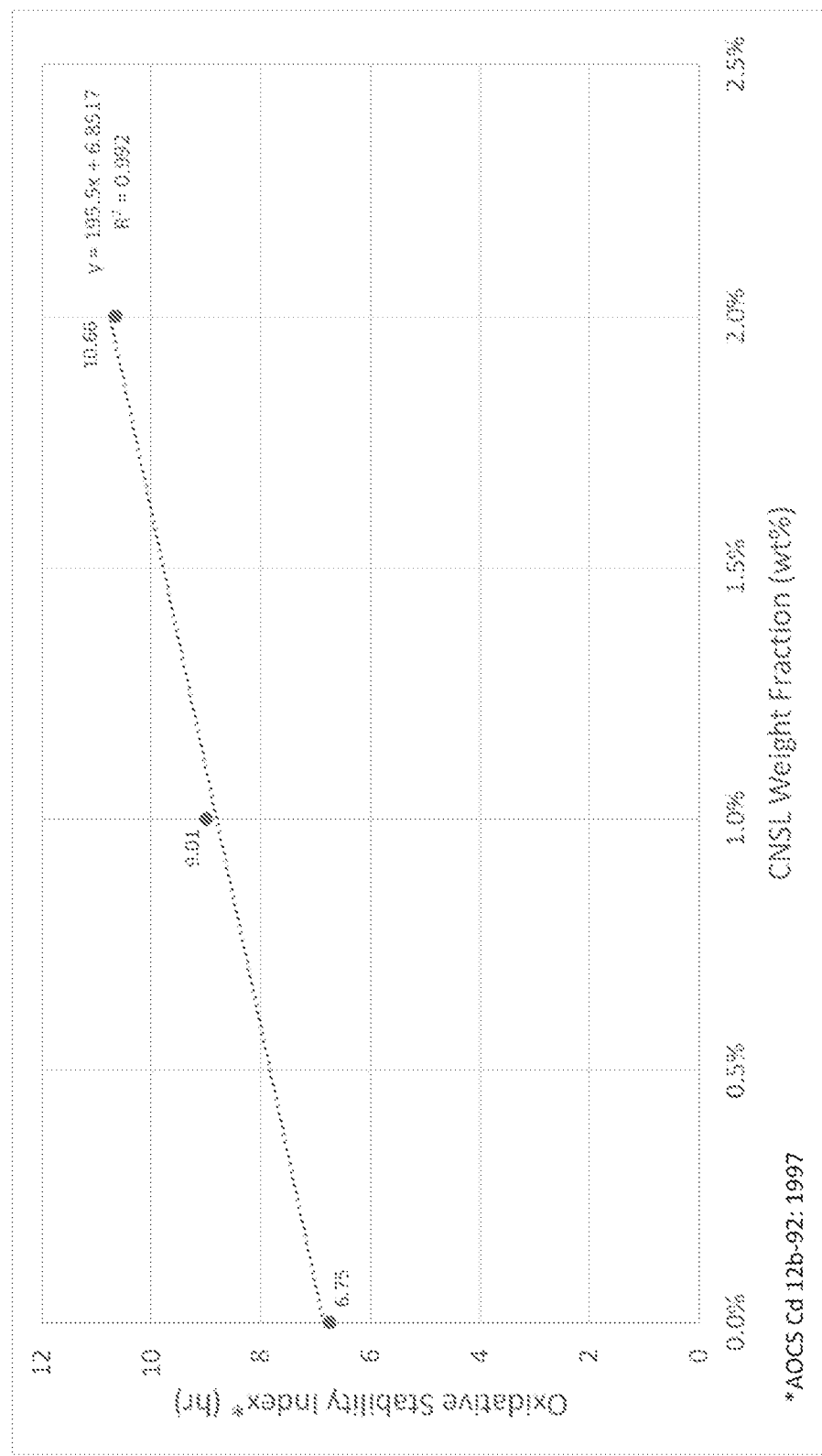
FIG. 5 is a graph showing results of oxidative stability tests in connection with Example 3.

A blend of fats, oils, and greases (FOG) comprising used cooking oil was subjected to oxidative stability test with and without CNSL inclusion. Distilled CNSL was added to the FOG at 1 and 2 wt. % concentrations in the blended feedstock. These two samples were submitted, along with a sample of the same FOG with no CNSL, for oxidative stability test according to AOCS Test Method Cd 12b-92. The tests were conducted at 110° C.
The results are presented in FIG. 5. As observed in FIG. 5, the oxidative stability increased from an induction time of 6.7 h (with no CNSL) to 10.7 h (with 2% CNSL).

Having thus described the invention in connection with the preferred embodiments thereof, it will be evident to those skilled in the art that various revisions can be made to the preferred embodiments described herein without departing from the spirit and scope of the invention. It is my intention, however, that all such revisions and modifications that are evident to those skilled in the art will be included with in the scope of the following claims.

The invention claimed is:

1. A lipid having a fused phenol group attached to the second and third carbon from the carboxylic acid carbon of a fatty acid molecule according to Structure II, with C3-C18 carbon chain including carbon-carbon double bonds, wherein the phenolic lipid is used as a hydrodeoxygenation feedstock for renewable diesel and wherein the lipid is optionally decarboxylated prior to the hydrodeoxygenation step.

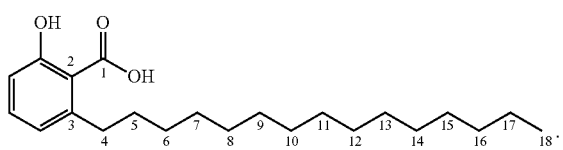

(II)

2. A method for producing a renewable diesel fuel comprising the steps of:
   a. combining a phenolic lipid and a hydrocarbon diluent to provide a hydrocarbon-diluted phenolic lipid;
   b. subjecting the hydrocarbon-diluted phenolic lipid to hydrodeoxygenation in a reactor to provide a reactor effluent including a hydrodeoxygenated phenolic lipid; and
   c. separating the hydrodeoxygenated phenolic lipid from the reactor effluent;
   d. wherein the hydrodeoxygenated phenolic lipid is a hydrocarbon with an oxygen content of less than 0.1 wt. %.

3. The method of claim 2 wherein the reactor includes a sulfided molybdenum catalyst and operates at a temperature between 600 and 650° F. in the presence of hydrogen under a pressure in the range of 500 to 2700 psig.

4. The method of claim 2, wherein the phenolic lipid is Cashew Nut Shell Liquid (CNSL).

5. The method of claim 2, wherein the phenolic lipid is blended with a non-phenolic lipid.

6. The method of claim 2, wherein the phenolic lipid is diluted with a paraffinic hydrocarbon.

7. The method of claim 6, wherein the volumetric ratio of the phenolic lipid to the paraffinic hydrocarbon is between 1:1 and 1:4.

8. The method of claim 2, wherein the phenolic lipid is partially hydrogenated.

9. The method of claim 2, wherein the sulfided molybdenum catalyst comprises a nickel or a cobalt promoter.

10. The method of claim 2, wherein the hydrodeoxygenated phenolic lipid has a bromine index greater than 70.

11. The method of claim 2, wherein the hydrodeoxygenated phenolic lipid is a hydrocarbon in the diesel boiling range (150-380° C.).

12. The method of claim 11, wherein the hydrocarbon has less than 4 wt. % mono-aromatic hydrocarbons no detectable polyaromatic hydrocarbons.

13. The method of claim 10, wherein the hydrocarbon comprises C21 hydrocarbons.

14. The method of claim 10, wherein the hydrocarbon comprises alkylcyclohexane.

15. The method of claim 10, wherein the hydrocarbon is used as a fuel or fuel component for compression ignition engines.

16. The method of claim 10, wherein the hydrocarbon is not isomerized.

17. The method of claim 15, wherein the hydrocarbon has a cloud point of 16° C. or less.

18. A renewable diesel (RD) fuel, comprising;
   a. n-alkyl cyclohexane compounds;
   b. less than 0.1 wt. % oxygen;
   c. a bromine index of 70 or higher;
   d. mono-aromatics content in the range of 1 wt. % to 4 wt. %; and
   e. no detectable di-, tri-or polyaromatics;
   f. wherein the n-alkyl cyclohexane compounds are the product of the hydrodeoxygenation of Cashew Nut Shell Liquid.

19. A method for storing electricity comprising the steps of;
a. directing the electricity to an electrolyzer for splitting a water stream into a hydrogen and an oxygen stream;
b. supplying the hydrogen to a batch reactor containing a phenolic lipid;
c. subjecting the phenolic lipid to hydrodeoxygenation in the batch reactor;
d. discharging a hydrodeoxygenated phenolic lipid from the batch reactor; and
e. wherein the hydrodeoxygenated phenolic lipid is a hydrocarbon with an oxygen content of less than 0.1 wt. %.

20. The method of claim 2, wherein the phenolic lipid is decarboxylated prior to hydrodeoxygenation.

21. A blended feedstock for hydrodeoxygenation comprising a phenolic lipid and a conventional lipid wherein;
a. the phenolic lipid is $2^{nd}$ boil Cashew Nut Shell Liquid;
b. the conventional lipid comprises at least 5 wt. % free fatty acid; and
c. the blended feedstock has a higher oxidative stability than the conventional lipid.

22. The method of claim 21, wherein the blended feedstock has a Rancimat induction time greater than 10 h as measured at 110° C. test temperature.

23. A method for producing a low sulfur diesel comprising biomass, comprising the steps of;
a. providing a combined feed comprising a petroleum diesel (straight run, light gas oil, light cycle oil, or light vacuum gas oil) with 0.1-1.3 wt. % sulfur and a phenolic lipid;
b. hydrotreating the combined feed in a hydrotreater comprising CoMo and/or NiMo catalyst; and
c. recovering a hydrotreated diesel fuel with less than 15 wppm sulfur;
d. wherein the combined feed includes up to 20 wt. % decarboxylated phenolic lipid and the decarboxylated phenolic lipid is $2^{nd}$ boil Cashew Nut Shell Liquid.

* * * * *